United States Patent [19]

Inskip et al.

[11] Patent Number: 4,638,079

[45] Date of Patent: Jan. 20, 1987

[54] INHIBITING POLYMERIZATION OF ETHYLENICALLY UNSATURATED MONOMERS

[75] Inventors: Ervin B. Inskip, Troy, Ill.; Joseph M. Patane, Manchester, Mo.

[73] Assignee: Mallinckrodt, Inc., St. Louis, Mo.

[21] Appl. No.: 692,080

[22] Filed: Jan. 17, 1985

[51] Int. Cl.[4] ........................ C07C 67/62; C07C 51/50
[52] U.S. Cl. ........................................ 560/4; 562/489; 562/490; 562/491; 562/492; 562/496; 562/595; 562/598; 585/5
[58] Field of Search ................ 585/5; 560/4; 562/489, 562/490, 491, 492, 496, 595, 598

[56] References Cited

U.S. PATENT DOCUMENTS

| | | | |
|---|---|---|---|
| 3,344,135 | 9/1967 | Middleton | 560/4 X |
| 3,426,063 | 2/1969 | Gros | 560/4 X |
| 4,210,493 | 7/1980 | Stewart et al. | 560/4 X |
| 4,310,676 | 1/1982 | Schropp | 560/4 |
| 4,507,495 | 3/1985 | Dougherty et al. | 560/205 |

*Primary Examiner*—Natalie Trousof
*Assistant Examiner*—Vera C. Clarke
*Attorney, Agent, or Firm*—R. G. Jackson; L. N. Goodwin; R. J. Klostermann

[57] ABSTRACT

Disclosed is a process for inhibiting polymerization of polymerizable ethylenically unsaturated monomers such as hydrocarbons, acids and esters, wherein a cobalt (III), nickel (II) or manganese (II) complex of N-nitrosophenylhydroxylamine is employed. A composition including a polymerizable ethylenically unsaturated monomer and the complex is also disclosed. In a preferred embodiment, polymerization of an acrylic acid or an acrylate ester is inhibited.

25 Claims, No Drawings

INHIBITING POLYMERIZATION OF ETHYLENICALLY UNSATURATED MONOMERS

This invention relates to a process for inhibiting polymerization of polymerizable ethylenically unsaturated monomers such as hydrocarbons, acids and esters, wherein a particular metal complex of N-nitrosophenylhydroxylamine is employed. The invention also relates to a composition including a polymerizable ethylenically unsaturated monomer and the metal complex.

Polymerizable ethylenically unsaturated monomers such as hydrocarbons, acids and esters undesirably polymerize at various stages of their manufacture, processing, handling, storage and use. A particularly troublesome problem is equipment fouling caused by polymerization in the purification stages of monomer production processes. Polymerization, such as thermal polymerization, during the purification of monomers results in the loss of monomeric material and in loss of production efficiency because the polymer often deposits in or on equipment in contact with the monomers and must be removed at frequent intervals.

A wide variety of substances have been proposed heretofore for inhibiting uncontrolled polymerization, e.g., thermal polymerization, of the above ethylenically unsaturated monomers. However, the heretofore proposed substances have not been entirely satisfactory. Accordingly, there is a substantial need in the art for improved processes for inhibiting polymerization of such monomers.

DESCRIPTION OF THE INVENTION

It has now unexpectedly been found that particular cobalt, nickel and manganese complexes of N-nitrosophenylhydroxylamine are effective inhibitors of undesired polymerization of ethylenically unsaturated monomers such as unsaturated hydrocarbons, hydrocarbyl acids and hydrocarbyl esters.

Generally stated, in one aspect of the present invention there is provided a process for inhibiting polymerization of a polymerizable ethylenically unsaturated monomer selected from the group consisting of polymerizable ethylenically unsaturated hydrocarbons, polymerizable ethylenically unsaturated acids and polymerizable ethylenically unsaturated esters, which comprises admixing therewith 0.001–0.5 part by weight per 100 parts by weight of the monomer of at least one metal complex of N-nitrosophenylhydroxylamine having the formula $MA_n$ where M is a cation selected from cobalt (III), nickel (II) and manganese II, A is the anion of N-nitrosophenyl hydroxylamine and n is a number equal to the valence of M.

In another aspect, generally stated this invention provides a composition comprising a mixture of the above ethylenically unsaturated monomer and metal complex in an amount effective for inhibiting thermal polymerization of the monomer. The composition of the invention may be stored, handled, used as monomeric material in polymerization processes, and otherwise processed with continuing inhibition of thermal polymerization therein.

DETAILED DESCRIPTION OF THE INVENTION AND OF THE MANNER AND PROCESS OF MAKING AND USING IT

The metal complex employed in this invention is preferably prepared by adding to an aqueous solution of a salt of the cation M, an aqueous solution containing the stoichiometric equivalent amount of the ammonium salt of N-nitrosophenylhydroxylamine. The resulting solid metal complex, which is essentially insoluble in water, may then be recovered by well known solid-liquid separation procedures, preferably filtration, followed by washing with water and drying. Preferred salts of the cation are cobalt (III) nitrate, nickel (II) nitrate and manganese (II) sulfate for preparing the complexes of cobalt (III), nickel (II) and manganese (II), respectively.

By employing these complexes or mixtures of two or more of them, undesired polymerization, such as thermal polymerization, may be inhibited in a wide variety of polymerizable ethylenically unsaturated hydrocarbons, acids and esters. Polymerizable ethylenically unsaturated hydrocarbons which may be employed in this invention include olefins in general, especially alpha olefins containing about 2–20 carbon atoms and preferably 2–8 carbon atoms and conjugated di-olefins, preferably those containing 4–6 carbon atoms such as butadiene, isoprene, and 2,3-dimethyl butadiene, and aromatic hydrocarbons having one or more side chains with ethylenic unsaturation contining, for example, 2–8 carbon atoms.

Suitable ethylenically unsaturated aromatic hydrocarbons include styrene, alpha vinylnaphthalene and p-divinylbenzene.

Suitable ethylenically unsaturated acids include acrylic acid and methacrylic acid. Suitable ethylenically unsaturated esters include the acrylates such as aklyl esters of acrylic acid and an alkanol having from one to about 8 carbon atoms and alkyl esters of methacrylic acid and an alkanol having from one to about 8 carbon atoms.

The acrylate esters advantageously may be an acrylic acid ester of methyl, ethyl, butyl or 2-ethylhexyl alcohol or a methacrylic acid ester of such alcohols.

Mixtures of the above ethylenically unsaturated monomers may be employed. For example, styrene may be admixed in any desired ratio with butadiene or p-divinyl benzene and thermal polymerization inhibited therein in accordance with the invention. It is understood that the above polymerizable ethylenically unsaturated hydrocarbons, acids and esters are merely given as examples of monomers for use in practicing the present invention, and that other suitable ethylenically unsaturated hydrocarbons, acids and esters may be used.

Preferably a complex is employed which is soluble in the composition containing the monomer to be inhibited; however, this is not necessary for acceptable results. Advantageously, the complexes employed in this invention are soluble in a wide variety of organic materials, including toluene, dimethylformamide, methylisobutylketone, many of the ethylenically unsaturated monomers, for example, acrylic and methacrylic acid, acrylate and methacrylate esters such as methyl acrylate and methyl methacrylate, styrene, butadiene and p-divinylbenzene. Accordingly, the solid complex may be dissolved in the monomer to be inhibited for effecting the inhibition without requiring use of water, which is often required in practice as a carrier for other inhibitors such as the ammonium salt of N-nitrosophenylhydroxylamine. This renders the inhibitor complexes especially attractive for addition to acrylic and methacrylic acid and their esters in the final stages of recovery of such monomers in industrial processes for polymerization thereof. Addition of water is undesirable at such stages.

The most effective complex depends upon the particular monomer to be inhibited and the extent to which oxygen is present. As a general preference, the manganese complex is preferred where oxygen is present in amounts, albeit minor, often encountered in purification processes for some monomeric materials such as acrylic acid and acrylate esters. The manganese complex is preferred for inhibiting polymerization of these monomers under such conditions. Where oxygen is at least substantially absent, for example in nitrogen purged systems, the cobalt or nickel complex is generally preferred for most of the monomers, including the acrylic acids and acrylates.

The complex may be mixed with a monomer to be inhibited in any suitable manner, including for example, mixing the complex with a solid monomer, dissolving it along in a liquid monomer or forming a solution of the complex in a solubilizing amount of a solvent therefor, which may be a small quantity of the monomer, and adding the resulting solution to a quantity of the monomer to be inhibited. Monomer-complex mixtures may also be formed by forming the complex in situ in the monomer, for example by admixing stoichiometric amounts of the ammonium salt of N-nitrosophenylhydroxylamine and a cobalt (III), nickel (II) or manganese (II) salt with the monomer.

For inhibiting polymerization in monomer purification stages of industrial production processes, the complex advantageously and preferably is first dissolved in a small quantity of a solvent therefor which is the same as the monomer to be inhibited or compatible therewith. The resulting inhibitor solution is then dissolved in the in-process stream containing the monomer to be inhibited.

Advantageously, the complexes inhibit polymerization of the monomers in both the liquid and vapor phases thereof. This two-phase effectiveness of the complexes constitutes a significant advantage over the performance of heretofore known inhibitors in ethylenically unsaturated monomers.

While not intending to be bound by any theory of operation, it is believed that the complexes minimize or eliminate formation of polymerization initiating agents which often are formed in situ in ethylenically unsaturated monomers under a variety of conditions, including for example, the conditions encountered in a variety of industrial monomer recovery processes.

The polymerization-inhibiting complex is employed in an amount effective to reduce the rate of formation of undesirable polymer due to unactivated or uncatalyzed polymerization, including the rate of thermal polymerization, and the quantity may vary over wide ranges. In most instances there is no upper limit except as dictated by economics and the practical aspects. The lower limit may vary somewhat depending upon the specific complex and monomer employed. It is understood that the inhibitor need be added only in a small amount which is effective to reduce polymerization, such as thermal polymerization. For example, often 0.001 part to 0.005 part by weight of the inhibitor for each 100 parts by weight of monomer present gives very noticeable improvement. Usually, it is not practical to employ amounts greater than 0.1 part by weight for each 100 parts by weight of monomer, but when desired, larger amounts may be employed such as 0.2 part to 0.5 part by weight or more. About 0.005–0.1 part by weight and preferably about 0.01–0.05 part by weight of the inhibitor for each 100 parts by weight of monomer gives excellent results, but often about 0.01–0.02 part by weight of the inhibitor is the most practical level.

The present invention is further illustrated by the following non-limiting examples. All parts, percentages and other amounts given throughout this disclosure are by weight unless otherwise indicated.

EXAMPLES 1–5

These examples illustrate the use of nickel (II), cobalt (III) and manganese (II) complexes of N-nitrosophenylhydroxylamine as polymerization inhibitors and compares effectiveness with the ammonium salt thereof.

Polymerization bottles (60 ml. capacity) were charged with 15 ml. relatively fresh acrylic acid monomer. The complexes and the ammonium salt were added to the bottles in the quantity indicated in Table I.

The bottles were either sealed in the presence of air on sealed after a nitrogen sparge. Then the bottles were placed in oil baths maintained at the indicated elevated temperatures. The heated bottles were observed at frequent intervals and the time for maximum visible thickening of the acrylic acid was noted. The data thus obtained are recorded in Table I. Also shown therein are the typical times to maximum visible thickening of acrylic acid containing the indicated amount of phenothiazine (PTZ), which is widely used for inhibiting acrylic acid polymerization in monomer recovery systems of industrial acrylic acid polymerization processes. The acrylic acid in each example contained 200 parts per million of the monomethyl ether of hydroquinone, which was incorporated by the supplier and could not safely be removed.

TABLE I

| Ex. | System | Conc.[a] | In | 100° C.[b] | 120° C.[b] |
|---|---|---|---|---|---|
| 1 | Control (MEHQ) | 100 | Air | 1 hr. | ½ hr. |
| 2 | Ni(NPHA)$_2$ | 100[c] | N$_2$ | 122 | 101 |
|   |   |   | Air | 3½ | ½ |
| 3 | Co(NPHA)$_3$ | 100[c] | N$_2$ | 110 | 110 |
|   |   |   | Air | 1 | ½ |
| 4 | Mn(NPHA)$_2$ | 100[c] | N$_2$ | 17½ | 21 |
|   |   |   | Air | >290 | 128 |
| 5 | NPH[d] | 100 | N$_2$ | 200 | 150 |
|   |   |   | Air | 3 | 2 |
| 6 | Phenothiazine | 100 | N$_2$ | 12 | 7 |
|   |   |   | Air | 50 | 16 |

[a]ppm
[b]Time required for polymerization to occur - in hours
[c]100 ppm based on amount of NPHA present
[d]Ammonium salt of N—nitrosophenylhydroxylamine
NOTES:
(1) The term "NPHA" means the anion of N—nitrosophenylhydroxylamine.
(2) The term "MEHQ" means monomethyl ether of hydroquinone.

BEST MODE CONTEMPLATED

The best mode contemplated for carrying out this invention has been set forth in the above description, for example, by way of setting forth preferred materials and operating conditions, including but not limited to preferred ranges and values of amounts and other nonobvious variables material to successfully practicing the invention in the best way contemplated at the time of executing this patent application.

It is understood that the foregoing detailed description is given merely by way of illustration and that many modifications may be made therein without departing form the spirit of scope of the present invention.

What is claimed is:

1. A process for inhibiting polymerization of a polymerizable ethylenically unsaturated acid monomer, which comprises admixing therewith per 100 parts by weight of the monomer 0.001–0.5 part by weight of at least one metal complex of N-nitrosophenylhydroxylamine having the formula $MA_n$ where M is a cation selected from cobalt (III), nickel (II) and manganese (II), A is the anion of N-nitrosophenylhydroxylamine and n is a number equal to the valence of M.

2. The process of claim 1 wherein said metal complex is prepared by a method comprising adding to an aqueous solution of a salt of the cation an aqueous solution containing the stoichiometric equivalent amount of the ammonium salt of N-nitrosophenylhydroxylamine.

3. The process of claim 2 wherein said salt is selected from the group consisting of cobalt (III) nitrate, nickel (II) nitrate and manganese (II) sulfate.

4. The process of claim 1 wherein said monomer is an acrylic monomer selected from the group consisting of acrylic acid and methacrylic acid.

5. A composition comprising a mixture of a polymerizable ethylenically unsaturated acid monomer and per 100 parts by weight of the monomer 0.001–0.5 part by weight of at least one metal complex of N-nitrosophenylhydroxylamine having the formula $MA_n$ where M is a cation selected from cobalt (III), nickel (II) and manganese (II), A is the anion of N-nitrosophenylhydroxylamine and n is a number equal to the valence of M.

6. The composition of claim 5 wherein said metal complex is prepared by a method comprising adding to an aqueous solution of a salt of the cation an aqueous solution containing the stoichiometric equivalent amount of the ammonium salt of N-nitrosophenylhydroxylamine.

7. The composition of claim 6 wherein said salt is selected from the group consisting of cobalt (III) nitrate, nickel (II) nitrate and manganese (II) sulfate.

8. The composition of claim 5 wherein said monomer is an acrylic monomer selected from the group consisting of acrylic acid and methacrylic acid.

9. A process of inhibiting polymerization in the substantial absence of oxygen of a polymerizable ethylenically unsaturated ester monomer, which comprises admixing with said monomer per 100 parts by weight of the monomer 0.001–0.5 part by weight of at least one metal complex of N-nitrosophenylhydroxylamine having the formula $MA_n$ where M is the cobalt (III) cation, A is the anion of N-nitrosophenylhydroxylamine and n is 3.

10. The process of claim 9 wherein said monomer is an acrylic monomer selected from the group consisting of alkyl esters of acrylic acid and an alkanol having from one to about 8 carbon atoms and alkyl esters of methacrylic acid and an alkanol having from one to about 8 carbon atoms.

11. The process of claim 10 wherein said monomer is selected from the group consisting of the acrylic acid esters of alcohols selected from the group consisting of methyl, ethyl, butyl and 2-ethylhexyl alcohol and the methacrylic acid esters of said alcohols.

12. The process of claim 11 where said monomer is a methacrylic acid ester of said alcohols.

13. The process of claim 11 wherein said monomer is methyl methacrylate.

14. A process for inhibiting polymerization in the presence of air of a polymerizable ethylenically unsaturated acid monomer, which comprises admixing with said monomer, per 100 parts by weight of the monomer, 0.001–0.5 part by weight of at least one metal complex of N-nitrosophenylhydroxylamine having the formula $MA_n$ where M is the manganese (II) cation, A is the anion of N-nitrosophenylhydroxylamine and n is 2.

15. The process of claim 14 wherein said monomer is an acrylic monomer selected from the group consisting of acrylic acid and methacrylic acid.

16. The process of claim 15 wherein said monomer is acrylic acid.

17. The process of claim 14 wherein said admixing is effected in the presence of air.

18. A composition stabilized against polymerization in the substantial absence of oxygen, which comprises a polymerizable ethylenically unsaturated ester monomer and, per 100 parts by weight of the monomer, 0.001–0.5 part by weight of at least one metal complex of N-nitrosophenylhydroxylamine having the formula $MA_n$ where M is the cobalt (III) cation, A is the anion of N-nitrosophenylhydroxylamine and n is 3.

19. The composition of claim 18 wherein said monomer is an acrylic monomer selected from the group consisting of alkyl esters of acrylic acid and an alkanol having from one to about 8 carbon atoms and alkyl esters of methacrylic acid and an alkanol having from one to about 8 carbon atoms.

20. The composition of claim 19 wherein said monomer is selected from the group consisting of the acrylic acid esters of alcohols selected from the group consisting of methyl, ethyl, butyl and 2-ethylhexyl alcohol and the methacrylic acid esters of said alcohols.

21. The composition of claim 20 where said monomer is a methacrylic acid ester of said alcohols.

22. The composition of claim 20 wherein said monomer is methyl methacrylate.

23. A composition stabilized against polymerization in the presence of air, which comprises a polymerizable ethylenically unsaturated acid monomer and, per 100 parts by weight of the monomer, 0.001–0.5 part by weight of at least one metal complex of N-nitrosophenylhydroxylamine having the formula $MA_n$ where M is the manganese (II) cation, A is the anion of N-nitrosophenylhydroxylamine and n is 2.

24. The composition of claim 23 wherein said monomer is an acrylic monomer selected from the group consisting of acrylic acid and methacrylic acid.

25. The composition of claim 23 wherein said monomer is acrylic acid.

* * * * *